(12) United States Patent
Kim et al.

(10) Patent No.: US 10,545,328 B2
(45) Date of Patent: Jan. 28, 2020

(54) METHOD AND APPARATUS FOR PROCESSING IMAGE

(71) Applicants: SAMSUNG ELECTRONICS CO., LTD., Suwon-si (KR); University of Seoul Industry Cooperation Foundation, Seoul (KR)

(72) Inventors: Hojung Kim, Suwon-si (KR); Kichul Kim, Seoul (KR); Yongkyu Kim, Hwaseong-si (KR); Hongseok Lee, Seongnam-si (KR)

(73) Assignees: SAMSUNG ELECTRONICS CO., LTD., Suwon-si (KR); University of Seoul Industry Cooperation Foundation, Seoul (KR)

( * ) Notice: Subject to any disclaimer, the term of this patent is extended or adjusted under 35 U.S.C. 154(b) by 24 days.

(21) Appl. No.: 15/724,459

(22) Filed: Oct. 4, 2017

(65) Prior Publication Data

US 2018/0157024 A1  Jun. 7, 2018

(30) Foreign Application Priority Data

Dec. 6, 2016  (KR) .......................... 10-2016-0165175

(51) Int. Cl.
*G02B 21/36* (2006.01)
*G06T 7/00* (2017.01)
(Continued)

(52) U.S. Cl.
CPC ............ *G02B 21/367* (2013.01); *A61B 6/027* (2013.01); *G03H 1/0808* (2013.01); *G03H 1/16* (2013.01);
(Continued)

(58) Field of Classification Search
CPC ...... G06F 17/142; G06F 17/14; G06F 9/5066; G03H 1/0808; G03H 2226/02;
(Continued)

(56) References Cited

U.S. PATENT DOCUMENTS 5,053,983 A * 10/1991 Hyatt .................. B60R 16/0373
708/306
5,526,506 A * 6/1996 Hyatt .................. B60R 16/0373
711/111
(Continued)

FOREIGN PATENT DOCUMENTS

| JP | 2004206254 A | 7/2004 |
|---|---|---|
| KR | 101366116 B1 | 2/2014 |
| KR | 1020140125608 A | 10/2014 |

OTHER PUBLICATIONS

Lin Y.-T., et al., "Low-power variable-length fast Fourier transform processor", IEE Proceedings: Computers and Digital Techniq, IEE, GB, vol. 152, No. 4, Jul. 2005, pp. 499-506.
(Continued)

*Primary Examiner* — Aklilu K Woldemariam
(74) *Attorney, Agent, or Firm* — Sughrue Mion, PLLC

(57) ABSTRACT

An image processing apparatus includes a core configured to perform a fast Fourier transformation (FFT) operation on the image data, a memory configured to store data that is output by the core, and a controller configured to control the core to perform the FFT operation on the image data. The core is resettable based on an amount of the image data.

19 Claims, 10 Drawing Sheets

(51) Int. Cl.
*G03H 1/16* (2006.01)
*A61B 6/02* (2006.01)
*G03H 1/08* (2006.01)
*G03H 1/02* (2006.01)

(52) U.S. Cl.
CPC ... *G06T 7/0012* (2013.01); *G03H 2001/0224* (2013.01)

(58) Field of Classification Search
CPC ......... G03H 1/2294; G03H 2001/0228; G03H 2001/2271; G03H 2210/454; G03H 1/16; G03H 2001/0224; G03H 2210/30; G01S 19/254; G01S 19/30; G01S 15/8977; H04L 27/263; H04L 27/265; H04L 1/20; H04N 19/42; H04N 19/60; H04N 19/90; G06T 158/00; G06T 2200/04; G06T 7/0081; G06T 2207/20056; G06T 9/00; G06T 3/40; G06T 3/4084; G06T 5/00; G06T 11/006; G06T 2207/20024; G06T 9/007; G06T 1/60; G06T 15/00; G02B 21/367; G01R 33/5608; G06K 9/527; G05B 2219/34098; B60L 15/007; B60L 2240/526; H02M 3/3376
USPC ......... 382/299, 305, 280; 345/503, 582, 608
See application file for complete search history.

(56) References Cited

U.S. PATENT DOCUMENTS

| | | | | |
|---|---|---|---|---|
| 5,859,788 A * | 1/1999 | Hou | ........................ | G06T 9/007 708/400 |
| 5,974,178 A | 10/1999 | Kitayoshi | | |
| 6,333,743 B1 * | 12/2001 | Gossett | ..................... | G06T 1/20 345/503 |
| 6,940,807 B1 * | 9/2005 | Rezvani | ................ | G06F 17/142 370/210 |
| 8,294,749 B2 | 10/2012 | Cable | | |
| 9,342,486 B2 * | 5/2016 | Lloyd | ................... | G06F 17/142 |
| 2002/0057850 A1 * | 5/2002 | Sirohey | ................ | G06T 3/4084 382/299 |
| 2006/0143258 A1 * | 6/2006 | Teng | ..................... | G06F 17/142 708/404 |
| 2006/0253513 A1 * | 11/2006 | Wezelenburg | ........ | G06F 17/142 708/404 |
| 2009/0013021 A1 | 1/2009 | Jhang et al. | | |
| 2010/0172579 A1 * | 7/2010 | Reid | ................... | G06K 9/00228 382/165 |
| 2012/0179041 A1 * | 7/2012 | Nakagawa | ........... | A61B 5/0073 600/443 |
| 2013/0010550 A1 * | 1/2013 | Kim | ........................ | G11C 7/02 365/189.15 |
| 2014/0198995 A1 * | 7/2014 | Pau | ....................... | G06T 3/4092 382/280 |
| 2014/0211039 A1 * | 7/2014 | Herman | ................... | G06T 9/00 348/222.1 |
| 2015/0331834 A1 * | 11/2015 | Sabelkin | ................ | H04N 19/60 708/400 |
| 2015/0335237 A1 * | 11/2015 | Okada | .................... | A61B 3/102 351/208 |
| 2016/0041524 A1 | 2/2016 | Song et al. | | |
| 2016/0048948 A1 * | 2/2016 | Bajic | ..................... | G06T 3/4084 382/299 |
| 2017/0064333 A1 * | 3/2017 | Kim | ....................... | H04N 19/60 |

OTHER PUBLICATIONS

Communication dated Feb. 20, 2018, issued by the European Patent Office in counterpart European application No. 17203099.1.

* cited by examiner

METHOD AND APPARATUS FOR PROCESSING IMAGE

CROSS-REFERENCE TO RELATED APPLICATION

This application claims priority from Korean Patent Application No. 10-2016-0165175, filed on Dec. 6, 2016, in the Korean Intellectual Property Office, the disclosure of which is incorporated herein by reference in its entirety.

BACKGROUND

1. Field

Exemplary embodiments relate to a method and apparatus for processing an image.

2. Description of the Related Art

In the field of three-dimensional (3D) image technology, research has been actively conducted to develop apparatuses for realizing a high-definition hologram in real time by using a complex spatial light modulator (SLM) capable of simultaneously controlling the amplitude and phase of light.

To reproduce a hologram moving picture, a computer-generated hologram (CGH) has been used. Image processing apparatuses perform a very large number of calculations to calculate a hologram value for each location in a hologram plane. In this aspect, in order to express a point in space, image processing apparatuses need to perform a Fourier transform operation one time. To express an image of a space, image processing apparatuses need to perform as many Fourier transform operations as the number of corresponding pixels of the image.

Image processing apparatuses, such as televisions (TVs) and mobile devices, can process image data in order to reproduce a hologram image. In this case, the image processing apparatuses can perform Fourier transformation operations on the image data and reproduce an image by using the transformed data.

When the image processing apparatuses perform Fourier transformation operations, a large number of calculations are performed, which is time consuming. In particular, portable devices such as mobile devices are limited with respect to both size and available power. Thus, there is a demand for methods of reducing the number of calculations and the calculation time when image processing apparatuses perform Fourier transformation operations.

SUMMARY

Provided are methods and apparatuses for performing Fourier transformation operations on image data.

Additional aspects will be set forth in part in the description which follows and, in part, will be apparent from the description, or may be learned by practice of the presented exemplary embodiments.

According to an aspect of an exemplary embodiment, an image processing apparatus for performing a fast Fourier transformation (FFT) operation on image data includes a core configured to perform an FFT operation on the image data; a memory configured to store data that is output by the core; and a controller configured to control the core to perform the FFT operation on the image data, wherein the core is resettable based on an amount of the image data.

According to an aspect of another exemplary embodiment, an image processing method for performing a fast Fourier transformation (FFT) operation on image data includes determining an amount of the image data; setting a core based on the determined amount of image data; and controlling the core to perform a 1D FFT operation on the image data.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Exemplary embodiments now will be described more fully hereinafter with reference to the accompanying drawings.

Figure 1:
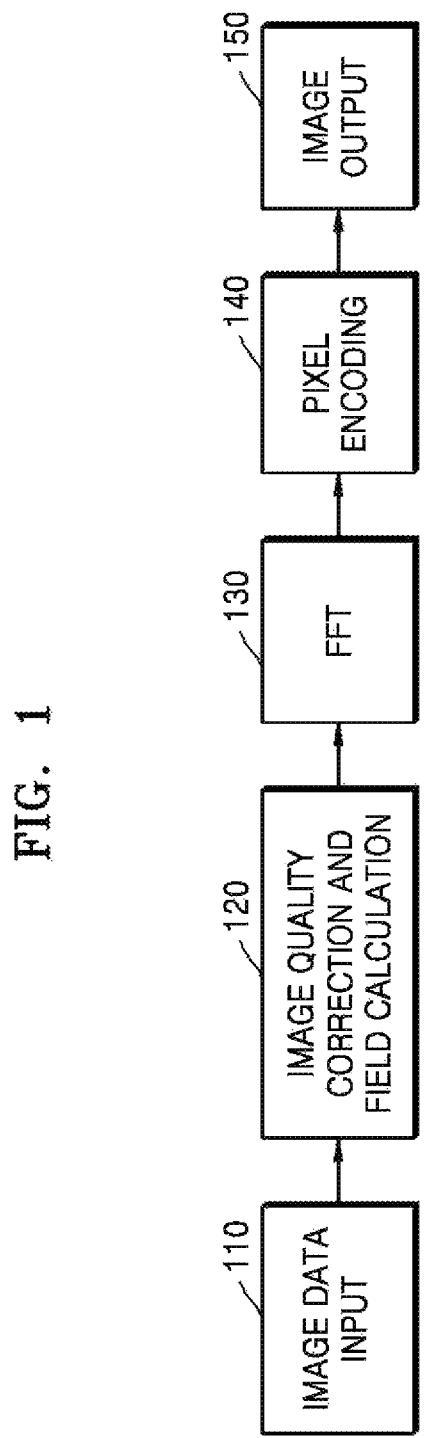
FIG. 1 is a schematic view illustrating a process of processing image data, according to an exemplary embodiment.

FIG. 1 is a schematic view illustrating a process of processing image data, according to an exemplary embodiment. Referring to FIG. 1, an image processing apparatus may receive image data and output an image on which image processing has been performed.

In operation 110, the image processing apparatus receives image data. For example, in computer-generated holography (CGH), when a layer-based algorithm is applied to image data, the image data may include color data (or a color image), depth data (or a depth image), or the like. The color data may include data that represents a plurality of colors for each plane of a plurality of planes. For example, the color data may include a red image, a blue image, and a green image. The layer-based algorithm is used to process data of each of the plurality of planes into which a reproduction area of a hologram is split based on depths. The image processing apparatus may generate a hologram image by performing a Fourier transform operation or an inverse Fourier transform operation on the data of each of the planes.

In operation 120, the image processing apparatus performs an image quality correction operation and a field calculation operation. The image processing apparatus may correct the image data in order to improve an image quality.

In operation 130, the image processing apparatus performs a Fourier transform operation or a fast Fourier transform (FFT) operation. For example, the image processing apparatus may perform a Fourier transform operation on a two-dimensional (2D) matrix type of image data. The image processing apparatus may perform a one-dimensional (1D) Fourier transform operation twice to accomplish a 2D Fourier transform. The image processing apparatus may perform a first 1D Fourier transform operation on the image data in a row direction and perform a second 1D Fourier transform operation on a result of the first 1D Fourier transform operation in a column direction. The image processing apparatus generates a hologram image via the Fourier transform operation.

The image processing apparatus may include a plurality of cores. The plurality of cores may be configured to perform a Fourier transform operation on the image data in parallel. For example, the image processing apparatus may allocate the image data of each plane to a respective one from among the plurality of cores, and each of the plurality of cores may perform a Fourier transform operation on the allocated image data.

A process in which the image processing apparatus performs a Fourier transform operation on the image data according to exemplary embodiments will be described below in detail with reference to FIGS. 2, 3, 4, 5, and 6.

In operation 140, the image processing apparatus performs a pixel encoding operation. The image processing apparatus generates data that is to be input to a screen, via the pixel encoding operation.

In operation 150, the image processing apparatus outputs an image to an image display.

Figure 2:
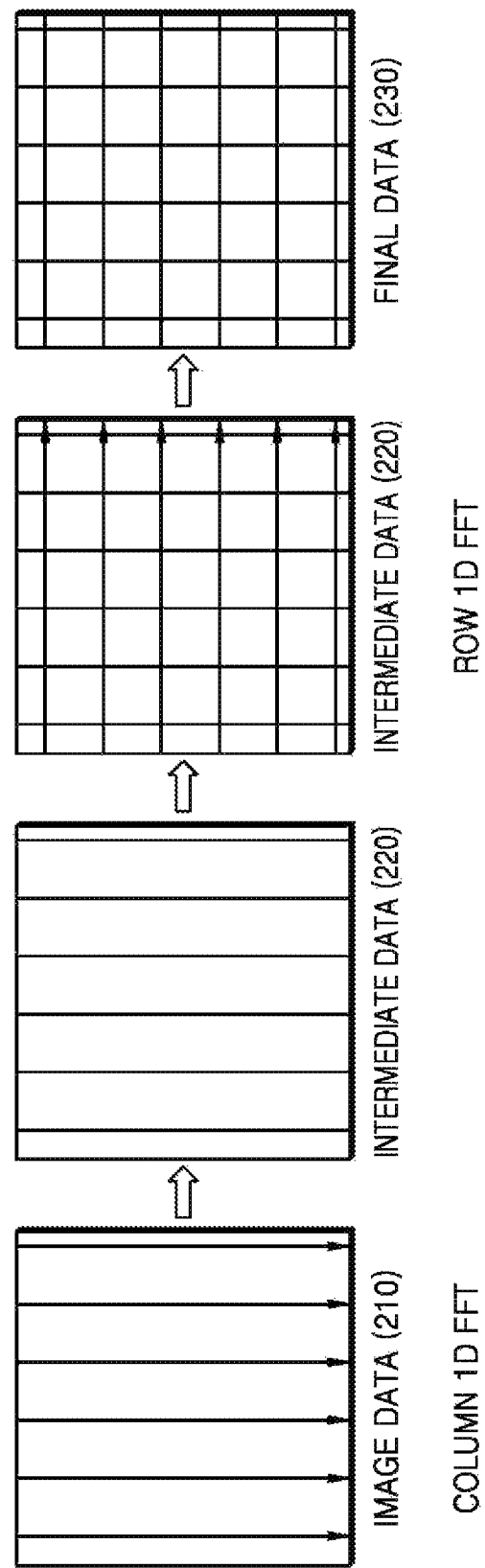
FIG. 2 illustrates a process of transforming data, according to an exemplary embodiment.

FIG. 2 illustrates a process of transforming data, according to an exemplary embodiment. Referring to FIG. 2, the image processing apparatus or a Fourier transform apparatus generates final data 230 by performing a 1D FFT operation twice on image data 210 (i.e., a primary 2D FFT operation). For example, the image processing apparatus performs a 1D FFT operation once on the image data 210 in the column direction to generate intermediate data 220, and then performs a 1D FFT operation once on the intermediate data 220 in the row direction to generate the final data 230. A secondary 2D FFT operation may also be achieved by performing a 1D FFT operation twice. The primary 2D FFT operation is an FFT operation from the pupil of a user to the retina of the user, and the secondary 2D FFT operation may be an FFT operation from a panel to the pupil.

The order of execution, in terms of column and row directions, of 1D FFT operations for the primary 2D FFT operation may be opposite to that of execution of 1D FFT operations for the secondary 2D FFT operation. For example, if 1D FFT operations are performed in the column direction and then in the row direction when a primary 2D FFT operation is performed, 1D FFT operations may be performed in the row direction and then in the column direction when a secondary 2D FFT operation is performed.

Figure 3:
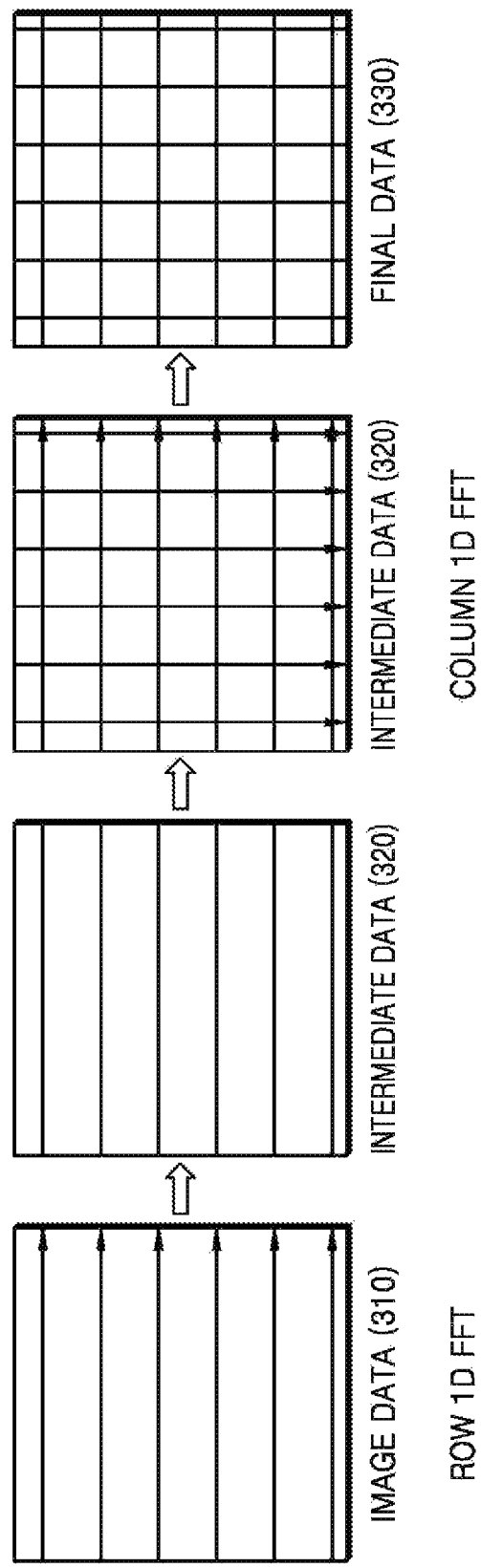
FIG. 3 illustrates a process of transforming data, according to another exemplary embodiment.

In FIG. 2, for example, a case in which the image processing apparatus performs a 1D FFT operation first in the column direction is described. In FIG. 3, for example, a case in which the image processing apparatus performs a 1D FFT operation first in the row direction is described.

Although only a case where a primary 2D FFT operation is performed is illustrated in FIGS. 2 and 3, a secondary 2D FFT operation may also be performed in the same manner as the primary 2D FFT operation or by changing the order of a row and a column.

The image processing apparatus performs a 1D FFT operation on the image data 210 in the column direction. The intermediate data 220 is data obtained by performing a 1D FFT operation on the image data 210 in the column direction. Arrows marked on the image data 210 indicate directions in which the image processing apparatus performs a 1D FFT operation. Straight lines marked on the intermediate data 220 indicate directions in which the image data 210 is transformed.

The image processing apparatus reads stored intermediate data 220 from a memory and performs a 1D FFT operation on the read intermediate data 220 in the row direction. When reading out the intermediate data 220 from the memory, the image processing apparatus may read out the intermediate data 220 in the row direction and output the read-out intermediate data 220 to each 1D FFT processor.

The image processing apparatus generates the final data 230 by performing a 1D FFT operation on the intermediate data 220 in the row direction. The final data 230 is data obtained as the image data 210 is 1D FFT-transformed respectively in the column direction and the row direction.

FIG. 3 illustrates a process of transforming data, according to another exemplary embodiment. Referring to FIG. 3, the image processing apparatus or a Fourier transform apparatus generates final data 330 by performing a 1D FFT operation twice on image data 310. For example, the image processing apparatus performs a 1D FFT operation once on the image data 310 in the row direction to generate intermediate data 320 and then performs a 1D FFT operation once on the intermediate data 320 in the column direction to generate the final data 330. In FIGS. 2 and 3, the order of a column and a row is switched and the description presented in FIG. 2 may be identically applied to the description of FIG. 3.

Figure 4:
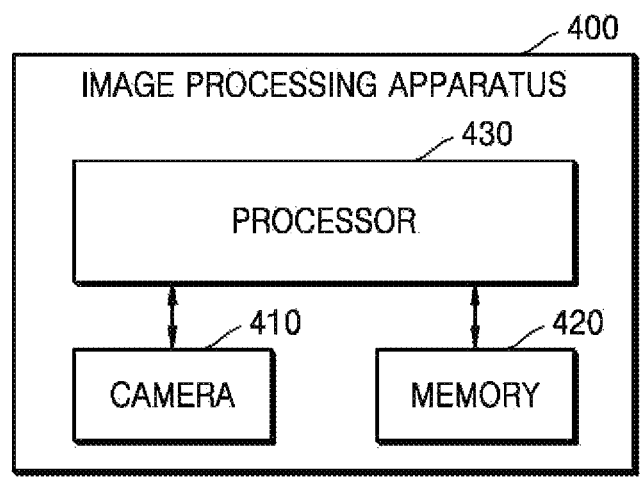
FIG. 4 is a block diagram of an image processing apparatus, according to an exemplary embodiment.

FIG. 4 is a block diagram of an image processing apparatus 400, according to an exemplary embodiment. Referring to FIG. 4, the image processing apparatus 400 may include a camera 410, a processor 430, and a memory 420. The image processing apparatus 400 may be any of an electronic apparatus (e.g., a computer, a mobile device, a display device, a wearable device, or a digital camera), a central processing unit (CPU), a graphic processing unit (GPU), or the like.

The camera 410 may capture an image and acquire a color image and a depth image from the captured image. The color image and the depth image are acquired in units of frames. The color image may be a composite image that includes a red image, a green image, and a blue image. Each of the red image, the green image, and the blue image is a single frame. The depth image is acquired for each color. In this aspect, the camera 410 acquires a depth image for the red image, a depth image for the green image, and a depth image for the blue image. The depth image for each of the red, green, and blue images is also a single frame.

The memory 420 stores the color image and the depth image. The memory 420 stores the frame generated by the processor 430.

Figure 5:
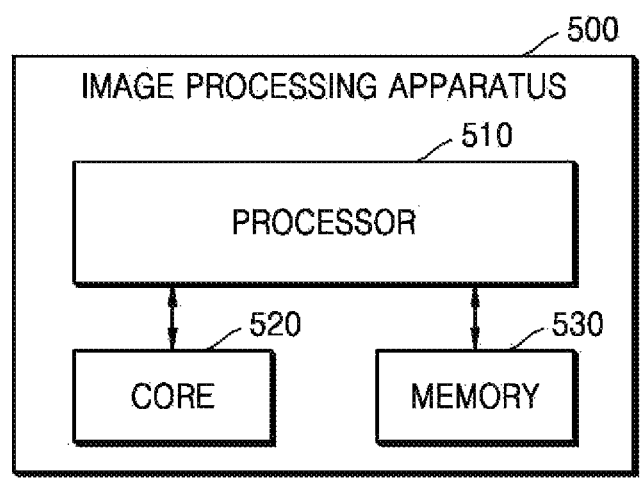
FIG. 5 is a block diagram of an image processing apparatus, according to another exemplary embodiment.

FIG. 5 is a block diagram of an image processing apparatus 500, according to another exemplary embodiment. The image processing apparatus 500 may be any of a mobile device, a display device, a wearable device, a CPU, a GPU, or the like.

The image processing apparatus 500 includes a controller (also referred to herein as a "processor") 510, a core 520, and a memory 530. The memory 530 may include dynamic random-access memory (DRAM) or static random-access memory (SRAM).

The controller 510 controls the core 520 and the memory 530. The controller 510 may determine data that is input to the core 520. The controller 510 may designate a calculation that is to be performed by the core 520. For example, the controller 510 may control the core 520 to perform a 1D FFT operation on data in the row direction, and may also control the core 520 to perform a 1D FFT operation on data in the column direction. The controller 510 may store data generated during a Fourier transformation operation in the memory 530.

The controller 510 controls the core 520 to perform a primary 2D FFT operation and a secondary 2D FFT operation on image data. The primary 2D FFT operation includes two 1D FFT operations, and the secondary 2D FFT operation includes two 1D FFT operations. The controller 510 may control the data that is input to the core 520, in order to perform a 2D FFT operation twice (i.e., to perform a primary 2D FFT operation and a secondary 2D FFT operation). The controller 510 controls a flow of data so that the core 520 performs a primary 2D FFT operation and then performs a secondary 2D FFT operation. Accordingly, the image processing apparatus 500 may perform a primary 2D FFT operation and a secondary 2D FFT operation (i.e., a total of four 1D FFT operations) by using the single core 520.

The controller 510 may reset the core 520. Resetting the core 520 may refer to changing the amount of data that is processible by the core 520. Resetting the core 520 may also refer to determining whether an FFT processor included in the core 520 is to operate. For example, the controller 510 may reset the core 520 so that the core 520 performs a 1K-POINT FFT operation or a 2K-POINT FFT operation. The controller 510 determines the amount of the data that is input to the core 520, based on the flow rate of the data, and determines whether FFT processors included in the core 520 are to operate, based on the determined amount of data.

The core 520 may Fourier-transform data included in each line of the frame. For example, the core 520 may perform a 1D FFT operation on the frame in a row direction. A single row or a single column may be referred to as a single line. The core 520 performing a 1D FFT operation on the frame in the row direction indicates performing a 1D FFT operation on pixel values included in the row of the frame.

The core 520 may output the data to the memory 530. Every time a result value obtained from performing a 1D FFT operation is generated, the core 520 may output the result value to the memory 530.

The core 520 may include a plurality of 1D FFT processors. The 1D FFT processors may perform a respective 1D FFT operation on each line of the frame.

The memory 530 may store and output the data. The memory 530 may include SDRAM or DRAM.

Figure 6:
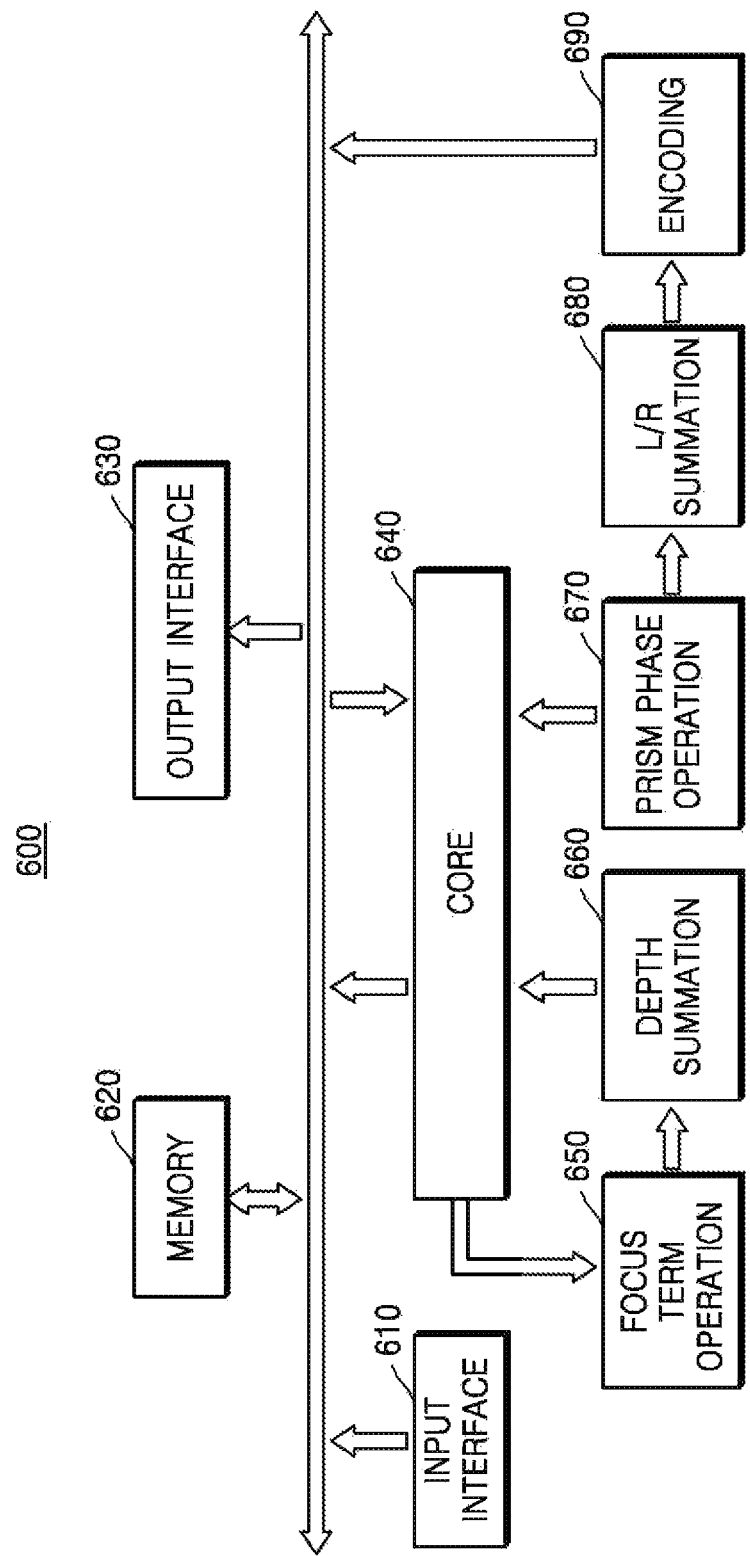
FIG. 6 is a block diagram for explaining a flow of processing data, according to an exemplary embodiment.

FIG. 6 is a block diagram for explaining a flow of processing data, according to an exemplary embodiment.

An input interface 610 receives image data. The image data may be transmitted to a memory 620 or a core 640 via a bus.

The memory 620 may store and output data. The memory 620 may include SDRAM or DRAM.

An output interface 630 outputs image data. The output interface 630 may be implemented as a display.

The core 640 may be reset based on the amount of the image data in order to perform an FFT operation on the image data.

The controller 510 controls a flow of the image data that is processed by an image processing apparatus 600, and resets the core 640 based on the amount of the image data that is input to the core 640.

Although not shown in FIG. 6, the image processing apparatus 600 may further include a plurality of operators. The plurality of operators may perform a focus term operation 650, a depth summation operation 660, a prism phase operation 670, a left-right (L/R) summation operation 680, and an encoding operation 690.

Figure 7:
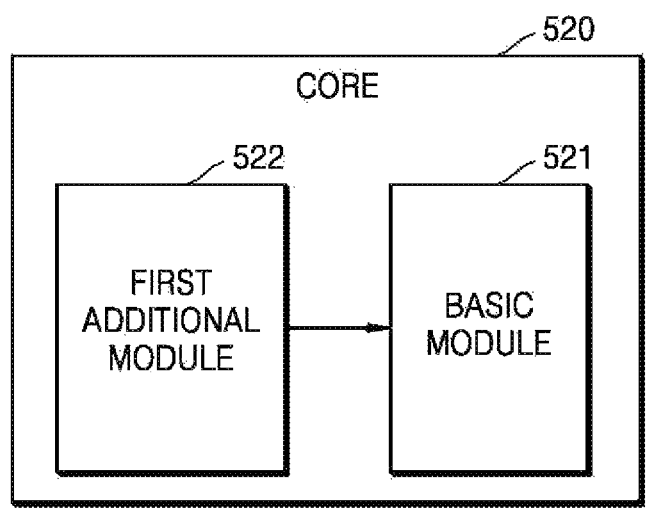
FIG. 7 is a block diagram of a core, according to an exemplary embodiment.

FIG. 7 is a block diagram of a core 520, according to an exemplary embodiment. Referring to FIG. 7, the core 520 may perform an FFT operation on image data of two amounts.

The amount of the image data may vary based on the size of a panel. For example, when the size of the panel is 1K×2K, the amount of the image data may be 1K×2K. In this case, the core 520 needs to perform a 1K FFT operation and a 2K FFT operation. When the size of a replacement panel is 2K×4K, the core 520 performs a 2K FFT operation and a 4K FFT operation.

In the core 520, according to a mode signal of the controller 510, only a basic module 521 may operate, or both a first additional module 522 and the basic module 521 may operate. Accordingly, the core 520 performs an FFT operation on image data of a first amount when only the basic module 521 operates, and performs an FFT operation on image data of a second amount when both the first additional module 522 and the basic module 521 operate.

The core 520 includes the first additional module 522 and the basic module 521. The basic module 521 includes a plurality of FFT processors. For example, one FFT processor may be a 2-POINT FFT processor. The first additional module 522 includes a single 2-POINT FFT processor. Whether the first additional module 522 is to operate may be determined under the control of the controller 510. Accordingly, when the first additional module 522 operates, the image data input to the first additional module 522 is transformed and then output to the basic module 521. Conversely, when the first additional module 522 does not operate, the image data input to the first additional module 522 is output to the basic module 521 without being transformed.

Figure 8:
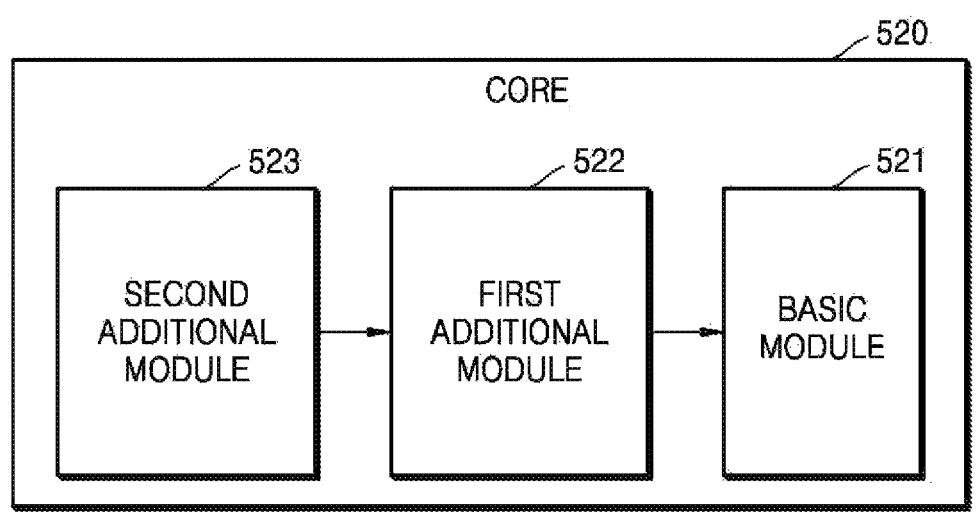
FIG. 8 is a block diagram of a core, according to an exemplary embodiment.

FIG. 8 is a block diagram of a core 520, according to an exemplary embodiment. Referring to FIG. 8, the core 520 may perform an FFT operation on image data of three amounts. Only the basic module 521 may operate, the first additional module 522 and the basic module 521 may operate, or a second additional module 523, the first additional module 522, and the basic module 521 may operate. Accordingly, the core 520 performs an FFT operation on image data of a first amount when only the basic module 521 operates; performs an FFT operation on image data of a second amount when the first additional module 522 and the basic module 521 operate; and performs an FFT operation on image data of a third amount when the second additional module 523, the first additional module 522, and the basic module 521 operate.

Although the core 520 that includes two additional modules, namely, the first and second additional modules 522 and 523, is illustrated in FIG. 8, the core 520 may include three or more additional modules, and may perform an FFT operation on image data of four or more amounts.

Figure 9:
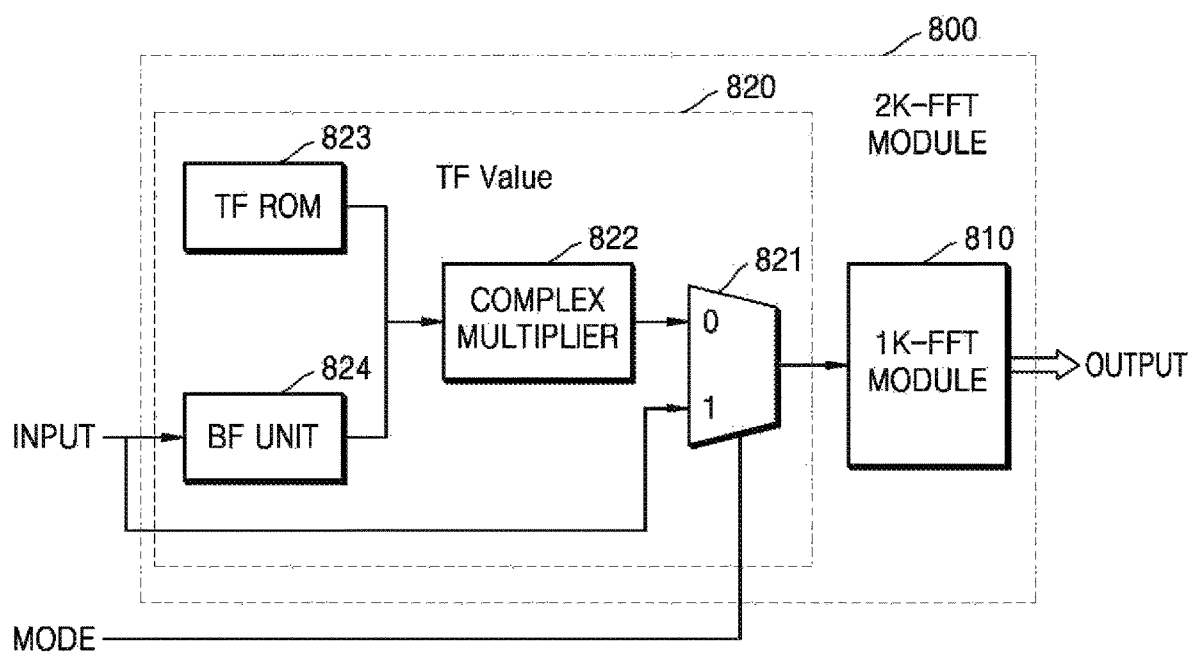
FIG. 9 is a block diagram of a core, according to an exemplary embodiment.

FIG. 9 is a block diagram of a core 800, according to an exemplary embodiment. Referring to FIG. 9, the core 800 is an example of a 2K-FFT module. The core 800 may control an additional module 820 to perform a 1K-FFT operation or a 2K-FFT operation.

For example, the additional module 820 performs a function of a 2-POINT processor. A 1K-FFT module 810 includes a plurality of 2-POINT processors or a plurality of 4-POINT FFT processors. For example, the 1K-FFT module 810 may include ten 4-POINT FFT processors.

Image data is input to the additional module 820. The image data is input to a ButterFly (BF) unit (also referred to herein as a ButterFly (BF) component) 824 and a multiplexer (MUX) 821 included in the additional module 820.

A mode signal is input to the MUX 821. A signal that is output by the MUX 821 varies based on the mode signal. For example, when the mode signal is one (1), the MUX 821 outputs the input image data to the additional module 820. When the mode signal is zero (0), the MUX 821 outputs image data obtained from a transformation operation performed by the additional module 820. In particular, when the mode signal is 0, the MUX 821 outputs data received from a complex multiplier 822.

A twiddle factor (TF) read-only memory (ROM) 823 outputs a TF value. The TF ROM 823 may include any of a shift register, a cache, a memory, or the like.

The BF unit 824 performs an FFT operation or an inverse FFT (IFFT) operation on the received image data. The BF unit 824 is controlled by a specific bit of an up-counter and constructs a single data path by using a Simple Dual-Port Block RAM (SDP-BRAM)-based delay feedback logic.

The complex multiplier 822 performs a complex multiplication operation on the TF value output by the TF ROM 823 and data output by the BF unit 824.

Whether the additional module 820 is to operate is determined based on the mode signal. According to whether the additional module 820 operates, a determination is made as to whether the core 800 is to operate as a 2K-FFT module or as a 1K-FFT module.

Figure 10:
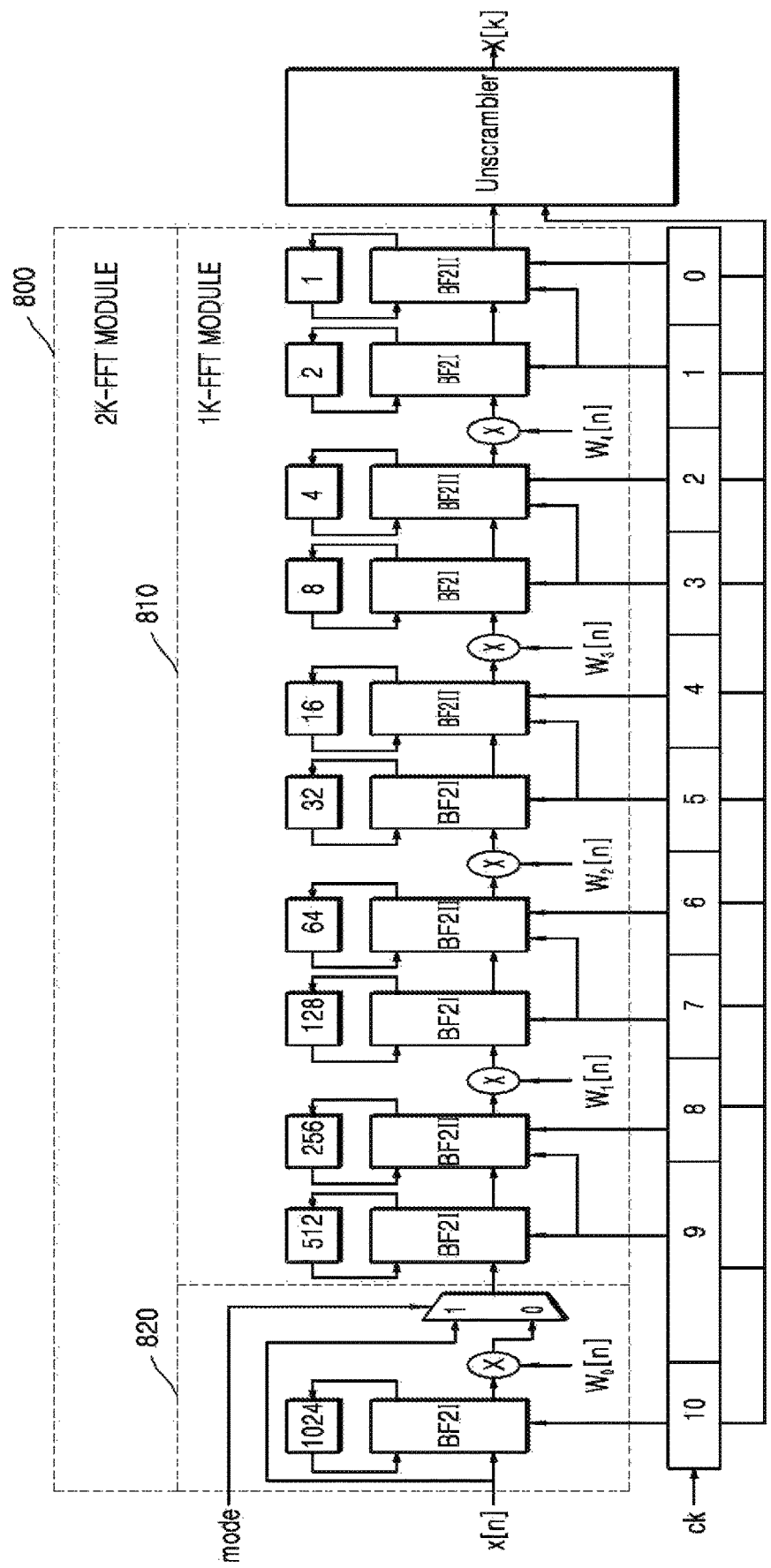
FIG. 10 is a block diagram of a core, according to an exemplary embodiment.

FIG. 10 is a block diagram of the core 800 of FIG. 9. FIG. 10 illustrates the core 800 of FIG. 9 in greater detail.

The 1K-FFT module 810 includes five 4-POINT FFT processors. Each 4-POINT FFT processor includes two BF units, two TR ROMs, and one complex multiplier. Each BF unit may be a BF2I component or a BF2II component. A clock signal is applied to each BF unit.

The additional module 820 includes the same components as those described above with reference to FIG. 9. The additional module 820 may be connected to a front end of the 1K-FFT module 810 and configured to determine the image data that is input to the 1K-FFT module 810. The additional module 820 may include the FFT processors included in the 1K-FFT MODULE 810 and a MUX, and may output image data and/or transformed image data.

Figure 11:
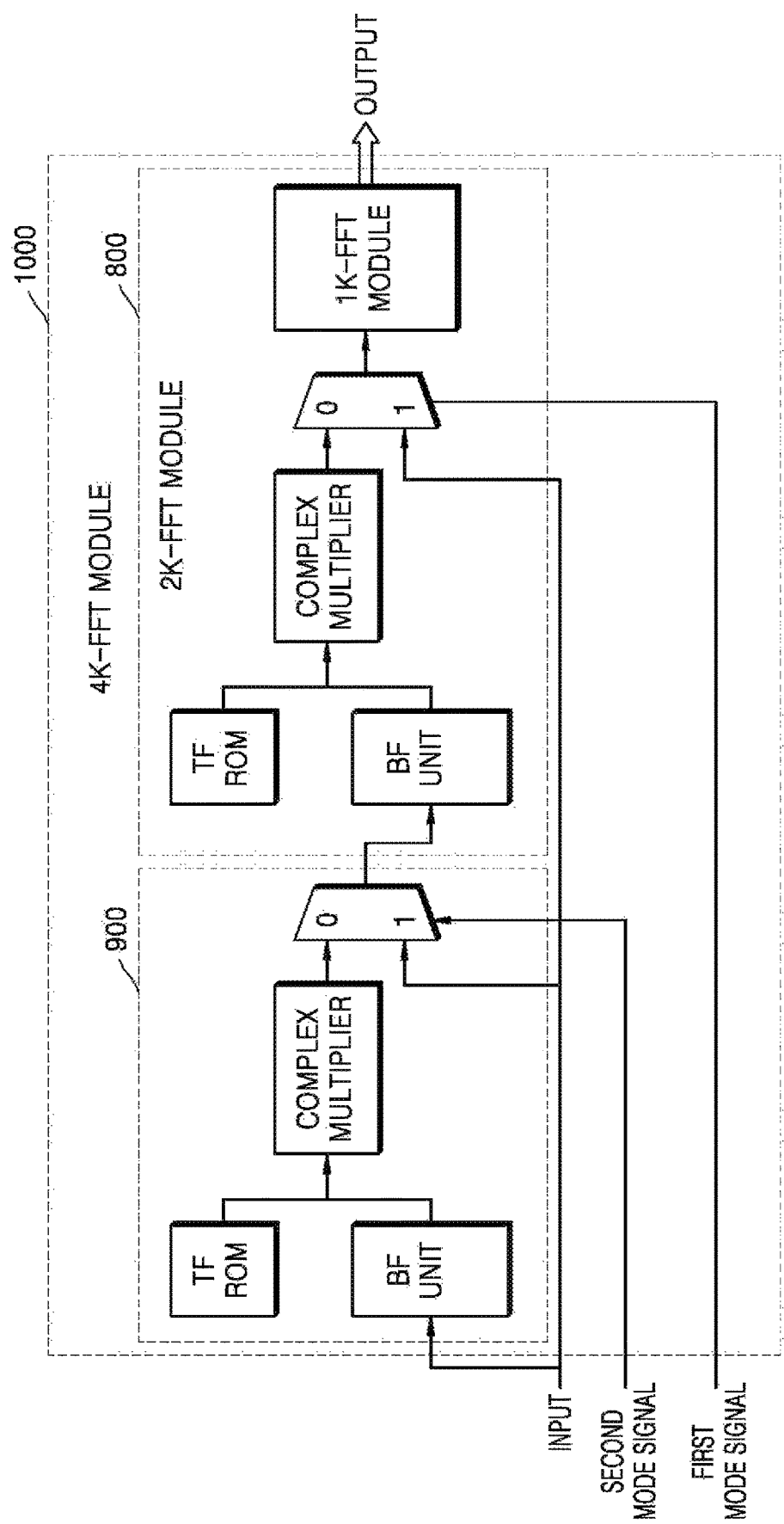
FIG. 11 is a block diagram of a core, according to an exemplary embodiment.

FIG. 11 is a block diagram of a core 1000, according to an exemplary embodiment. Referring to FIG. 11, the core 1000 is a detailed illustration of the core 520 of FIG. 8.

The core 1000 may process image data of three amounts. For example, the core 1000 may perform a 1K-POINT FFT operation, a 2K-POINT FFT operation, or a 4K-POINT FFT operation, wherein 1K, 2K, and 4K indicate amounts of image data.

Since the core 1000 includes two additional modules, whether the additional modules are to operate is determined based on respective amounts of data. When the amount of data is equal to 1K, a 1 is input as a first mode signal to a MUX of a 2K-FFT module 800. When the amount of data is equal to 2K, a 0 is input as the first mode signal to the MUX of the 2K-FFT module 800, and a 1 is input as a second mode signal to a MUX of an additional module 900. When the amount of data is equal to 4K, a 0 is input as each of the first and second mode signals to the MUXes of the 2K-FFT module 800 and the additional module 900.

Figure 12:
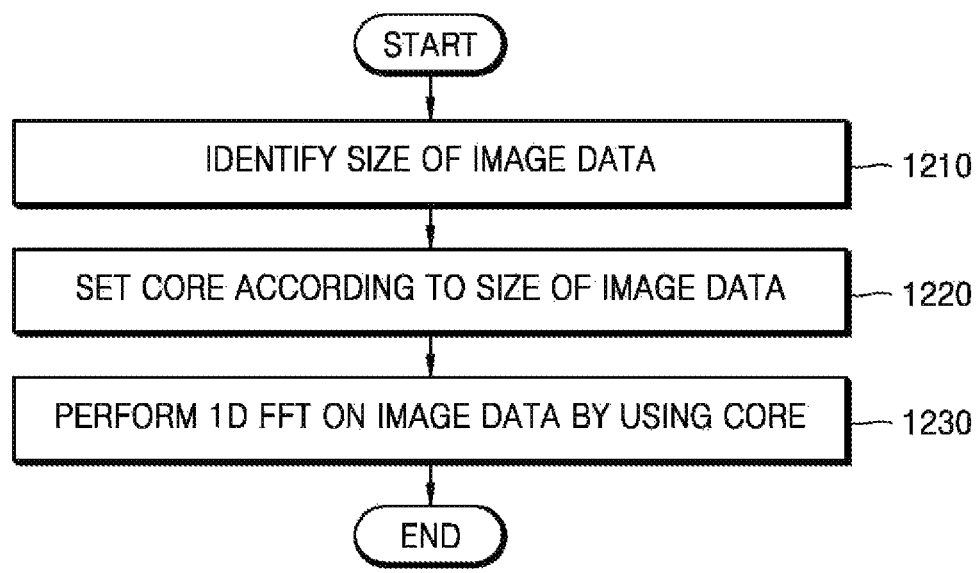
FIG. 12 is a flowchart of an image processing method, according to an exemplary embodiment.

FIG. 12 is a flowchart of an image processing method, according to an exemplary embodiment.

In operation 1210, an image processing apparatus determines the amount of image data. The amount of the image data may vary based on the size of a panel. The amount of the image data includes the sizes of rows and columns of the image data.

In operation 1220, the image processing apparatus sets a core based on the amount of the image data. The image processing apparatus sets the core based on the sizes of columns when performing an FFT operation on the image data in the row direction, and sets the core based on the sizes of rows when performing an FFT operation on the image data in the row direction. In particular, when rows×columns of the image data is equivalent to 1K×2K, the image processing apparatus needs to perform a 2K-POINT FFT operation in order to perform a FFT operation in the row direction (because the number of rows is equal to 1K, whereas one row includes data of 2K-POINT).

The image processing apparatus determines whether an additional module included in the core is to operate, and outputs a control signal (or mode signal) to the additional module based on the determination. A controller of the image processing apparatus may output a 0 or a 1 to a MUX included in the additional module and thus may determine output data of the MUX. For example, when a 1 is input to the MUX, the image data input to the additional module is output by the MUX. When a 0 is input to the MUX, the image data obtained from transformation performed by the additional module is output by the MUX.

The core of the image processing apparatus may include a basic module, a first additional module, and a second additional module. The image processing apparatus outputs the control signal to a MUX of the first additional module and a MUX of the second additional module based on the amount of the image data.

In operation 1230, the core of the image processing apparatus performs a 1D FFT operation on the image data.

According to an exemplary embodiment, the image processing apparatus may perform an FFT operation on image data even when the amount of the image data is changed by controlling an operation of the additional module.

According to an exemplary embodiment, the image processing apparatus may process various amounts of image data by using the additional module connected to the basic module.

The apparatuses described herein may comprise a processor, a memory configured for storing program data and executing a program that relates to the stored program data, a permanent storage unit such as a disk drive, a communications port configured for handling communications with external devices, and user interface devices, including a touch panel, keys, buttons, etc. When software modules or algorithms are involved, these software modules may be stored as program instructions or computer readable codes executable on a processor on a transitory or non-transitory computer-readable recording medium. Examples of the non-transitory computer-readable recording medium include magnetic storage media (e.g., read-only memory (ROM), random-access memory (RAM), floppy disks, hard disks, etc.), and optical recording media (e.g., compact disc-ROMs (CD-ROMs), or Digital Versatile Discs (DVDs)). The computer readable recording medium can also be distributed over network coupled computer systems so that the computer readable code is stored and executed in a distributive manner. This media can be read by the computer, stored in the memory, and executed by the processor.

Exemplary embodiments may be described in terms of functional block components and various processing steps. Such functional blocks may be realized by any number of hardware and/or software components configured to perform the specified functions. For example, exemplary embodiments may employ various integrated circuit (IC) components, e.g., memory elements, processing elements, logic elements, look-up tables, and the like, which may carry out a variety of functions under the control of one or more microprocessors or other control devices. Similarly, where the elements are implemented by using software programming or software elements, the exemplary embodiments described herein may be implemented with any programming or scripting language such as C, C++, Java, assembler language, or the like, with the various algorithms being implemented with any combination of data structures, objects, processes, routines or other programming elements. Functional aspects may be implemented by using algorithms that are executed on one or more processors. Furthermore, the exemplary embodiments described herein could employ any number of conventional techniques for electronics configuration, signal processing and/or control, data processing and the like. The words "mechanism," "element," "means," and "configuration" are used broadly and are not limited to mechanical or physical embodiments, but can include software routines in conjunction with processors, etc.

The particular implementations shown and described herein are illustrative examples and are not intended to otherwise limit the scope of the present inventive concept in any way. For the sake of brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical apparatus.

The use of the terms "a" and "an" and "the" and similar referents in the context of describing the exemplary embodiments (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The exemplary embodiments are not limited to the described order of the steps. The use of any and all examples, or exemplary language (e.g., "such as") provided herein, is intended merely to better illuminate the present inventive concept and does not pose a limitation on the scope of the present inventive concept unless otherwise claimed. Numerous modifications and adaptations will be readily apparent to one of ordinary skill in the art without departing from the spirit and scope of the present disclosure.

What is claimed is:

1. An image processing apparatus, comprising at least one processor to control:

a core configured to perform a fast Fourier transformation (FFT) operation on image data and output a final image data, the core comprising a basic module configured to perform the FFT operation on the image data having an amount that is equal to or less than 1 K, wherein 1K relating to a size of an image panel and an additional module configured to perform FFT operation on an image data having an amount that is greater than 1 K, wherein 1K relating to a size of an image panel;

a memory configured to store the final image data that is output by the core; and wherein the processor is further configured to control the core to perform the FFT operation on the input image data, determine an amount of the image data, and output a control signal that is usable for determining whether the additional module is to operate in addition to the basic module based on the amount of the image data, wherein the core is reset to change an amount of image data that is processable based on the amount of the image data, and wherein the image processing apparatus is configured to output an image to a display based on the final image data.

2. The image processing apparatus of claim 1, wherein the basic module is a 1K FFT module, when a 1K FFT operation is to be performed, the processor is further configured to control the additional module to stop operating so that the core performs the 1K FFT operation, and when a 2K FFT operation is to be performed, the processor is further configured to control the additional module to operate so that the core performs the 2K FFT operation.

3. The image processing apparatus of claim 1, wherein the additional module is connected to the basic module, and data to be output by the additional module is input to the basic module.

4. The image processing apparatus of claim 1, wherein the core further comprises a twiddle factor (TF) read-only memory (ROM), a butterfly (BF) component, a complex multiplier, and a multiplexer (UJX), and the processor is further configured to output a control signal to the MUX that is usable for determining a value that is to be output by the MUX.

5. The image processing apparatus of claim 1, wherein the processor is further configured to reset the core based on at least one from among a size of a row of the image data and a size of a column of the image data.

6. The image processing apparatus of claim 1, wherein the processor is further configured to reset the core based on an amount of data processed by the core.

7. The image processing apparatus of claim 1, wherein the additional module comprises a first additional module and a second additional module, the first additional module is connected to an input end of the basic module, and the second additional module is connected to an input end of the first additional module, each of the first additional module and the second additional module comprises a multiplexer (MUX), and the processor is further configured to output a control signal to each of the MUX of the first additional module and the MUX of the second additional module based on the amount of the image data.

8. An image processing method for performing a fast Fourier transformation (FFT) operation on image data, the image processing method comprising:

determining an amount of the image data;
setting a core based on the determined amount, the core including a basic module configured to perform the FFT operation on the image data having the amount that is equal to or less than 1K, wherein 1K relating to a size of an image panel and an additional module configured to perform FFT operation on the image data having the amount that is greater than 1K, wherein 1K relating to a size of an image panel; and
controlling the core to perform a 1D FFT operation on the image data and outputting a final image data; and
outputting an image to a display based on the final image data,
wherein the setting the core comprises determining whether the additional module included in the core is to operate in addition to the basic module included in the core based on the determined amount of the image data.

9. The image processing method of claim 8, wherein the determining the amount of the image data comprises determining a size of a column of the image data and determining a size of a row of the image data.

10. The image processing method of claim 8, wherein the setting the core comprises:
when a 1D FFT operation in a row direction is to be performed on the image data, setting the core based on a size of a column of the image data; and
when a 1D FFT operation in a column direction is to be performed on the image data, setting the core based on a size of a row of the image data.

11. The image processing method of claim 8, wherein the setting the core further comprises:
outputting a control signal to the additional module, based on a result of the determining.

12. The image processing method of claim 11, wherein the outputting the control signal comprises outputting one from among a zero and a one to a multiplexer (MUX) included in the additional module and determining output data of the MUX.

13. The image processing method of claim 8, wherein
the additional module includes a first additional module and a second additional module, and
the setting the core comprises outputting a control signal to each of a multiplexer (MUX) of the first additional module and a AMUX of the second additional module based on the amount of the image data.

14. A non-transitory computer-readable recording medium having recorded thereon a computer program which, when executed by a computer, performs the image processing method of claim 8.

15. An image processing apparatus, comprising at least one processor to control:
a core that includes two or more fast Fourier transformation (FFT) modules, each of the two or more FFT modules being configured to perform a respective FFT operation on input image data to output final image data based on an amount of the input image data; and
a memory configured to store the final image data that is output by the core,
wherein the processor is further configured to determine the amount of the input image data, to determine, for each of the two or more FFT modules, whether to operate the FFT modules together based on the determined amount of the input image data being greater than 1K, wherein 1K relating to a size of an image panel or to operate one of the two or more FFT modules based on the determined amount of the input image data being equal to or less than 1K, wherein 1K relating to a size of an image panel and to control each of the two or more FFT module with respect to whether the respective FFT operation is to be performed as a result of a corresponding determination, and
wherein the image processing apparatus is configured to output an image to a display based on the final image data.

16. The image processing apparatus of claim 15, wherein the two or more FFT module comprises a first FFT module and a second FFT module, and
when the determined amount of input image data is less than or equal to a threshold amount, the processor is further configured to determine that the first FFT module is to be operated and the second FFT module is not to be operated, and
when the determined amount of input image data greater than the threshold amount, the processor is further configured to determine that each of the first FFT module and the second FFT module is to be operated.

17. The image processing apparatus of claim 16, wherein
when a determination is made that the first FFT module is to be operated and the second FFT module is not to be operated, the processor is further configured to output a zero (0) to the first FFT module and to output a one (1) to the second FFT module, and
when a determination is made that that each of the first FFT module and the second FFT module is to be operated, the processor is further configured to output a zero (0) to each of the first FFT module and the second FFT module.

18. The image processing apparatus of claim 15, wherein the processor is further configured to determine a size of a row of the input image data and a size of a column of the input image data, and to determine the amount of the input image data based on at least one from among the determined row size and the determined column size.

19. The image processing apparatus of claim 15, further comprising at least one from among a focus term operator configured to perform a focus term operation on the data that is output by the core, a depth summer configured to perform a depth summation operation on the data that is output by the core, a prism phase operator configured to perform a prism phase operation on the data that is output by the core, a left-right summer configured to perform a left-right summation on the data that is output by the core, and an encoder configured to perform an encoding operation on the data that is output by the core.

* * * * *